(12) United States Patent
Werner

(10) Patent No.: US 10,330,224 B2
(45) Date of Patent: Jun. 25, 2019

(54) FLUID HOSE DEVICE

(71) Applicant: Medin Medical Innovations GmbH, Olching (DE)

(72) Inventor: Liselotte Werner, Olching (DE)

(73) Assignee: MEDIN MEDICAL INNOVATIONS GMBH, Olching (DE)

( * ) Notice: Subject to any disclaimer, the term of this patent is extended or adjusted under 35 U.S.C. 154(b) by 908 days.

(21) Appl. No.: 14/759,589

(22) PCT Filed: Nov. 25, 2013

(86) PCT No.: PCT/EP2013/074644
§ 371 (c)(1),
(2) Date: Jul. 7, 2015

(87) PCT Pub. No.: WO2014/108239
PCT Pub. Date: Jul. 17, 2014

(65) Prior Publication Data
US 2015/0345671 A1    Dec. 3, 2015

(30) Foreign Application Priority Data

Jan. 10, 2013 (EP) .................................. 13150731

(51) Int. Cl.
*F16L 11/11* (2006.01)
*A61M 16/00* (2006.01)
(Continued)

(52) U.S. Cl.
CPC .......... *F16L 11/11* (2013.01); *A61M 16/0057* (2013.01); *A61M 16/0875* (2013.01);
(Continued)

(58) Field of Classification Search
CPC .......... F16L 11/18; F16L 11/118; F16L 11/11; F16L 11/111; F16L 11/121
(Continued)

(56) References Cited

U.S. PATENT DOCUMENTS 3,578,777 A * 5/1971 DeGain ..................... F16L 9/06
138/121
3,605,877 A * 9/1971 Bauman et al. ....... G08C 19/12
165/267
(Continued)

FOREIGN PATENT DOCUMENTS

EP          2514478 A1    10/2012
WO          WO9639999     12/1996

OTHER PUBLICATIONS

European Search Report corresponding to European Application No. 13150731.1, dated Jun. 13, 2017 (5 pages).

*Primary Examiner* — Patrick F Brinson
(74) *Attorney, Agent, or Firm* — Maginot, Moore & Beck, LLP

(57) ABSTRACT

The present invention relates to a fluid hose device (1) comprising a fluid hose (2), through which a fluid can be transported, having a plurality of anti-kink projections (3) which are spaced apart from one another and provided in the longitudinal direction (L) of the fluid hose (1), which projections extend in a circular manner around the external surface (7) of the fluid hose (2), wherein a group (9) of a plurality of connecting webs (4) is provided in each case between two adjacent anti-kink projections (3), which webs interconnect the adjacent anti-kink projections (3), wherein the groups (9) are arranged in an alternating chevron pattern in the longitudinal direction (L) of the fluid hose (1).

19 Claims, 8 Drawing Sheets

(51) Int. Cl.
*A61M 39/08* (2006.01)
*F16L 11/12* (2006.01)
*A61M 16/08* (2006.01)

(52) U.S. Cl.
CPC ............ *A61M 39/08* (2013.01); *F16L 11/111* (2013.01); *F16L 11/121* (2013.01); *A61M 2207/00* (2013.01)

(58) Field of Classification Search
USPC ........................................ 138/121, 122, 173
See application file for complete search history.

(56) References Cited

U.S. PATENT DOCUMENTS

| | | | |
|---|---|---|---|
| 3,858,615 A | | 1/1975 | Weigl |
| 4,500,284 A | * | 2/1985 | Lupke ................ B29C 47/0023 156/244.14 |
| 4,745,881 A | | 5/1988 | Larson |
| 5,439,035 A | * | 8/1995 | Dal Palu e,acu uAttilio ............. F16L 11/118 138/121 |
| 5,706,864 A | * | 1/1998 | Pfleger ...................... B32B 1/08 138/121 |
| 6,755,217 B1 | * | 6/2004 | Yoshida ................ F16L 11/112 138/121 |
| 7,089,965 B2 | * | 8/2006 | Cheng ...................... F16L 11/11 138/121 |
| 7,232,597 B2 | * | 6/2007 | Iwata ........................ B32B 1/08 428/36.9 |
| 8,096,326 B2 | * | 1/2012 | Palmeri ................ F16L 11/118 138/121 |
| 2006/0118114 A1 | | 6/2006 | Hinkle |

\* cited by examiner

FLUID HOSE DEVICE

PRIORITY CLAIM

This application is a 35 U.S.C 371 National Stage application of PCT/EP2013/074644, filed Nov. 25, 2013, which claims the benefit of prior European Application No. 13150731.1 filed Jan. 10, 2013. The entire contents of the above-mentioned patent applications are incorporated herein by reference as part of the disclosure of this U.S. application.

FIELD OF THE INVENTION

The present invention relates to a fluid hose device, in particular for ventilators.

TECHNICAL BACKGROUND

A ventilator or respirator is an electric machine, today controlled by microprocessors, or a pneumatically driven machine for providing respiration for people whose own breathing is insufficient or has stopped. The respiratory gas is usually oxygenated. Depending on the field of application, a distinction is made between emergency, intensive care and home respirators. Anaesthetic machines are also specialised ventilators.

In ventilators, the respiratory gases are supplied to and returned from the person via fluid lines. Fluid lines of this kind are ideally lightweight and flexible, so as to achieve the greatest possible comfort for the patients.

Thin-walled fluid lines are known in the prior art which enclose helical reinforcement ribs intended to make the line more resistant to being crushed or becoming obstructed while still permitting a lightweight and flexible design of the fluid line.

DE 603 02 303 T2 discloses a line of this kind, comprising: at least one thin plastics material tape having a forward and a trailing side edge, the tape being arranged in a helical manner, the surface thereof being substantially parallel to the spiral axis, and the forward edge of each revolution of the tape overlapping, apart from at its ends, with the trailing edge of a previous revolution, and the trailing edge of each revolution of the tape underlapping the forward edge of a subsequent revolution, and a reinforcing bead of plastics material, which is arranged in the vicinity of the forward edge and between overlapping forward and trailing edges in each case, characterised in that the overlapping edge meets or substantially meets the underlapping tape at one edge of the bead.

DE 20 2012 007 386 U1 discloses a corrugated pipe for receiving supply lines of a medical installation, comprising an undulating inner pipe made of a first material and a tubular outer casing made of a second material, the outer casing forming a frictional connection or an interlocking connection with the inner pipe, at least at the peaks of the crests of the undulations of the inner pipe.

The fluid lines described above require many method steps during the production thereof and are therefore very expensive. Furthermore, these fluid lines have some tendency to kink since they have less dimensional stability and kink when a minimum bend radius is not reached. In addition, the fluid lines described above are somewhat inflexible and rigid, which is undesirable.

This is a situation which needs to be improved.

SUMMARY OF THE INVENTION

In this context, the object of the present invention is to provide a fluid hose device which is simple to produce and which has a reduced tendency to kink, while still being flexible.

According to the invention, this object is achieved by a fluid hose device having the features of claim 1.

According thereto, the following is provided:

A fluid hose device comprising a fluid hose, through which a fluid can be transported, having a plurality of anti-kink projections which are spaced apart from one another and provided in the longitudinal direction of the fluid hose, which projections extend in a circular manner around the external surface of the fluid hose, wherein a group of a plurality of connecting webs is provided in each case between two adjacent anti-kink projections, which webs interconnect the adjacent anti-kink projections, wherein the groups are arranged in an alternating chevron pattern in the longitudinal direction of the fluid hose.

The present invention is based on the concept of increasing the dimensional stability of a fluid hose device by means of anti-kink projections which extend in a circular manner around the external surface of a fluid hose. A further increase in the dimensional stability is achieved according to the invention by means of the connecting webs, which interconnect the anti-kink projections. The desired and legally required flexibility and dimensional stability of the fluid hose is additionally achieved in that the individual groups of the connecting webs are provided in an alternating pattern in the longitudinal direction of the fluid hose. The pattern in which the connecting webs are provided in the longitudinal direction of the fluid hose can be adjusted and changed according to the field of application and the constraints. In addition, said fluid hose device is particularly simple to produce since it requires a minimal number of elements and can advantageously be produced by means of a simple injection moulding method.

Advantageous embodiments and developments can be found in the further dependent claims and in the description with reference to the figures of the drawings.

According to one embodiment, the groups comprise two connecting webs which are arranged so as to be offset from one another by 180°. According to a further embodiment, the groups are arranged so as to be angularly offset by 90° in each case. Due to this configuration, the bending behaviour of the fluid hose device is angle-independent.

According to a further embodiment, the groups comprise n connecting webs, which are arranged so as to be offset from one another by 360°/n, n being a natural number greater than or equal to 3. A person skilled in the art may change the number n according to the constraints and the field of application in order to increase or decrease the flexibility and dimensional stability of the fluid hose device.

According to a further advantageous embodiment, the groups are arranged so as to be angularly offset by 360°/2n in each case, n being a natural number greater than or equal to 3.

According to a further preferred embodiment, the anti-kink projections and/or the connecting webs are formed in one piece with the fluid hose. The production costs for the fluid hose device can thus be reduced, since the fluid pipe device can be produced by means of an injection moulding method.

According to a further embodiment of the invention, the anti-kink projections are arranged so as to be equidistant and in parallel. For example, the anti-kink projections are arranged at a spacing of from 0.2 mm-5 mm from one another. The spacing of the anti-kink projections from one another, as well as the axial length of the connecting webs, for example of between 0.1 mm-3 mm, can also be adjusted according to the field of application and the desired dimensional stability.

According to a further embodiment, the anti-kink projections and the connecting webs extend at the same height, beginning at the external surface of the fluid hose. For example, the anti-kink projections and the connecting webs extend from the external surface of the fluid hose by from 0.2 mm to 2 mm. The height of the anti-kink projections and the connecting webs also influences the dimensional stability and the bending behaviour of the fluid hose device.

According to a further embodiment, the fluid hose or fluid hose device is a plastics material injection-moulded part made of a thermoplastic, e.g. TPE-s. However, the fluid hose device may also be made of another plastics material, for example an elastomer or a fibre-reinforced plastics material.

According to a further embodiment, the inside of the fluid hose is formed so as to be substantially planar. In this way, the fluid can be transported particularly well in the fluid hose.

According to a further embodiment, the connecting webs comprise high-tensile-strength fibres. The bending behaviour of the fluid hose device can be additionally influenced by means of this configuration.

According to a further embodiment, the fluid hose is formed of a first plastics material and the anti-kink projections and the connecting webs are formed of a second plastics material which is different from the first plastics material.

According to a further embodiment, the anti-kink projections and the connecting webs are configured such that the fluid hose device has angle-independent bending behaviour.

According to a further embodiment, a fluid hose device according to the invention is used in a ventilator, in particular in a CPAP ventilator.

The above embodiments and developments can, as far as is appropriate, be combined with one another in any desired manner. Further possible embodiments, developments and implementations of the invention also include combinations, which are not explicitly mentioned, of features of the invention which are described above or in the following with reference to the embodiments. In particular, in the process, a person skilled in the art will also add individual aspects as improvements or supplements to the respective basic form of the present invention.

DESCRIPTION OF THE DRAWINGS

The present invention will be described in greater detail in the following, with reference to the embodiments shown in the schematic figures of the drawings, in which.

Figure 1:
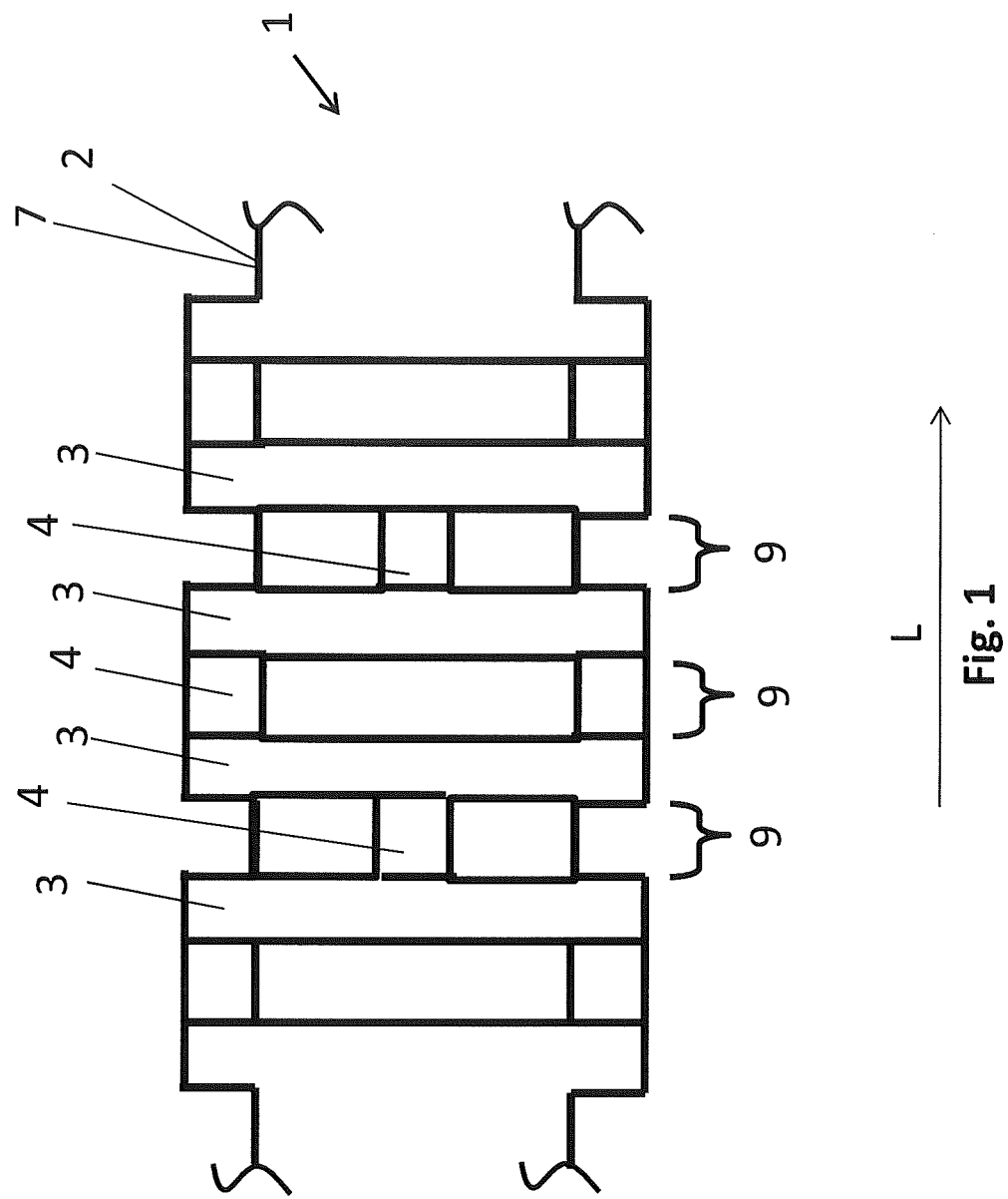
FIG. 1 is a schematic plan view of an embodiment of a fluid hose device.

The accompanying drawings are intended to improve comprehension of the embodiments of the invention. They show embodiments and, in conjunction with the description, explain principles and concepts of the invention. Other embodiments and many of the stated advantages emerge with reference to the drawings. The elements in the drawings are not necessarily shown to scale with respect to one another.

In the figures of the drawings, identical elements, features and components and those having the same function and effect are each provided with the same reference numerals, unless stated otherwise.

DESCRIPTION OF EMBODIMENTS

FIG. 1 is a schematic plan view of an embodiment of a fluid hose device 1. The fluid hose device 1 comprises a fluid hose 2, through which a fluid can be transported. The fluid may be a respiratory gas for example, which is used for providing respiration for a patient. The fluid hose may be formed for example from a thermoplastic and/or an elastomer.

A plurality of anti-kink projections 3, 11 are provided on the fluid hose 2, which projections are arranged in the longitudinal direction L of the fluid hose 2. The anti-kink projections are arranged in parallel with one another and so as to be spaced apart from one another at regular intervals. The anti-kink projections extend in a circular manner around the external surface 7 of the fluid hose 2. When the fluid hose 2 is bent, adjacently arranged come into contact with one another and thereby prevent further bending of the fluid hose 2.

A group 9 of a plurality of connecting webs 4, 10 is provided between two adjacent anti-kink projections 3, 11, which webs interconnect the adjacent anti-kink projections 3, 11. According to the invention, the groups 9 are arranged in an alternating chevron pattern in the longitudinal direction L of the fluid hose 1. The dimensional stability of the can be increased and the susceptibility to kinking reduced thereby.

According to this embodiment, the groups comprise in each case two connecting webs 4, 10, which are arranged so as to be offset from one another by 90° or 180°. The adjacently provided groups 9 of connecting webs may, however, also be provided at 15°, 30°, 45°, 60°, 105° and/or 120° to one another.

In general terms, the groups 9 can comprise n connecting webs 4, 10, which are arranged so as to be offset from one another by 360°/n, n being a natural number greater than or equal to 3.

The groups 9 may also be arranged so as to be angularly offset by 360°/2n in each case, n being a natural number greater than or equal to 3.

Figure 2:
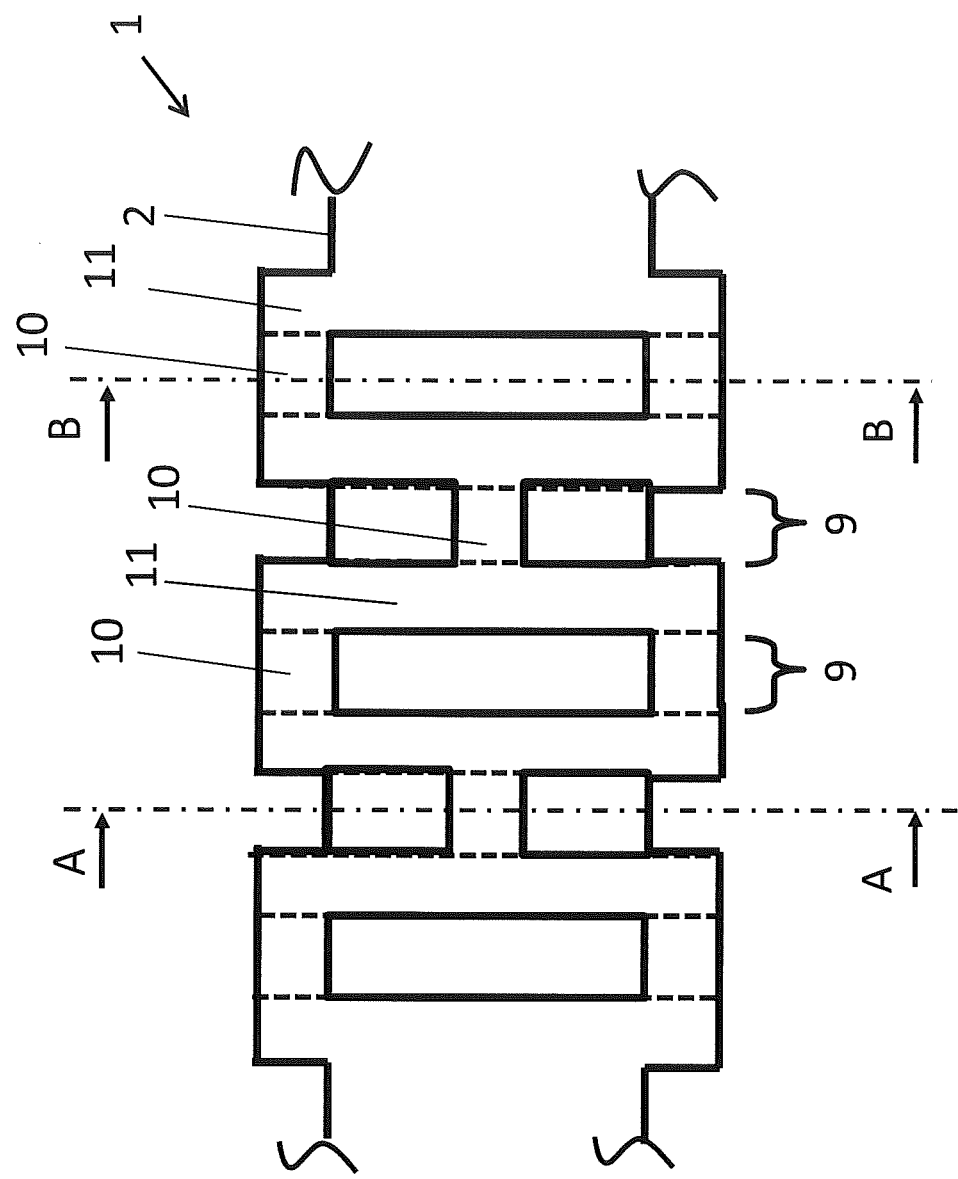
FIG. 2 is a schematic plan view of a further embodiment of a fluid hose device.

FIG. 2 is a schematic plan view of a further embodiment of a fluid hose device 1. According to this embodiment, the anti-kink projections 3, 11 and/or the connecting webs 4, 10 are formed in one piece with the fluid hose 2. The fluid hose device 1 can thereby be designed very cost-effectively, since the fluid hose device can be produced in an injection moulding method.

The individual anti-kink projections 3, 11 are arranged according to this embodiment so as to be equidistant and in parallel. However, it is also possible to arrange the anti-kink projections 3 with irregular spacing from one another in order to thereby be able to change the flexibility of the fluid hose device 1 and adjust it to specific constraints.

Figure 3:
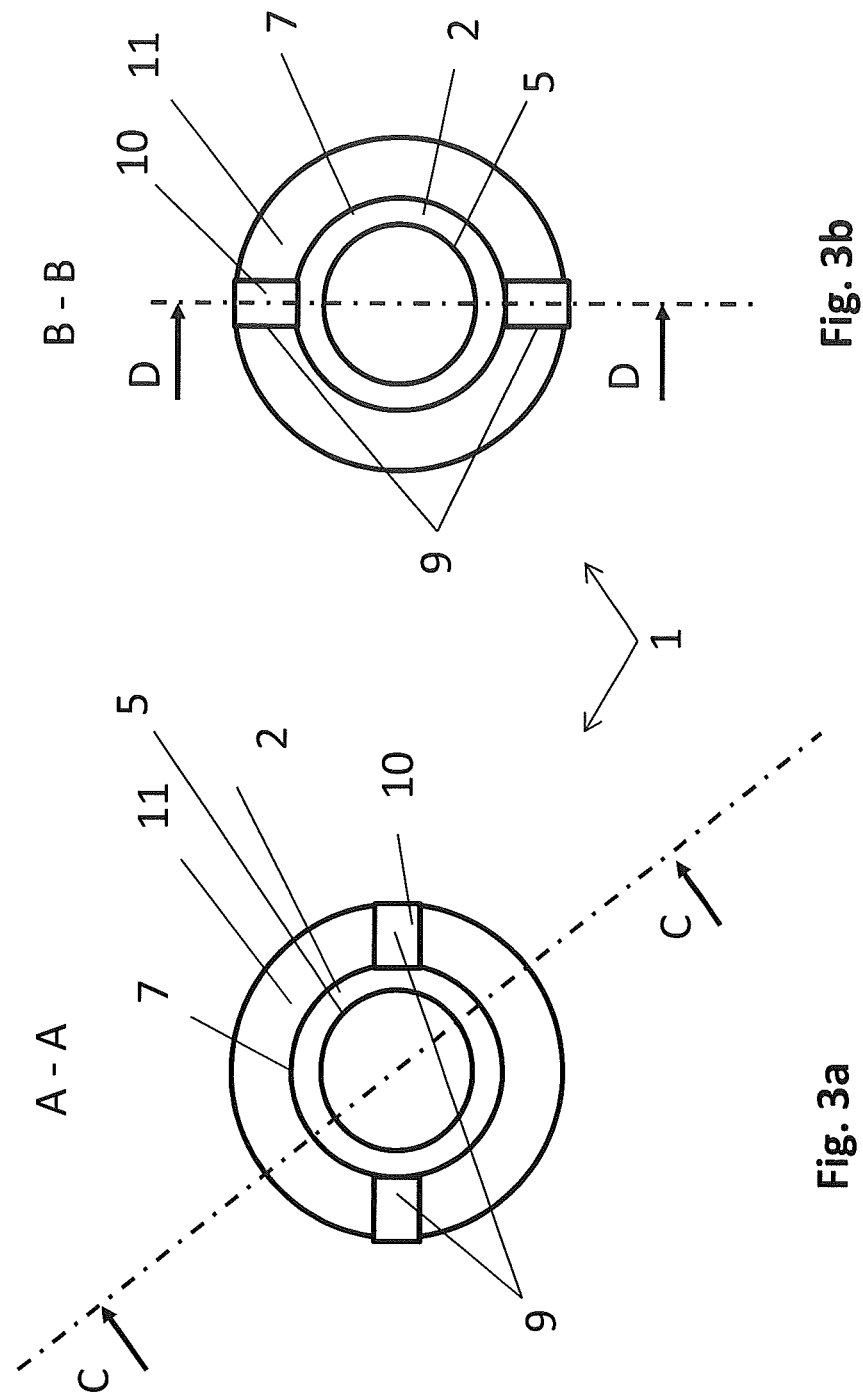
FIG. 3a, 3b are two schematic sectional views of an embodiment of a fluid hose device.

FIGS. 3a and 3b are two schematic sectional views of an embodiment of a fluid hose device 1. The extension of the sections A-A and B-B is shown in FIG. 2. As can be seen from FIGS. 3a and 3b, the adjacent groups 9 of connecting webs 10 are arranged so as to be offset from one another by an angular dimension. In the embodiment shown, this is 90°. The embodiment shown comprises two connecting webs 4 per group 9, which webs interconnect the anti-kink projections 3 arranged adjacently to one another. The connecting webs are provided in a mutually opposing manner on the fluid hose 2.

Figure 4:
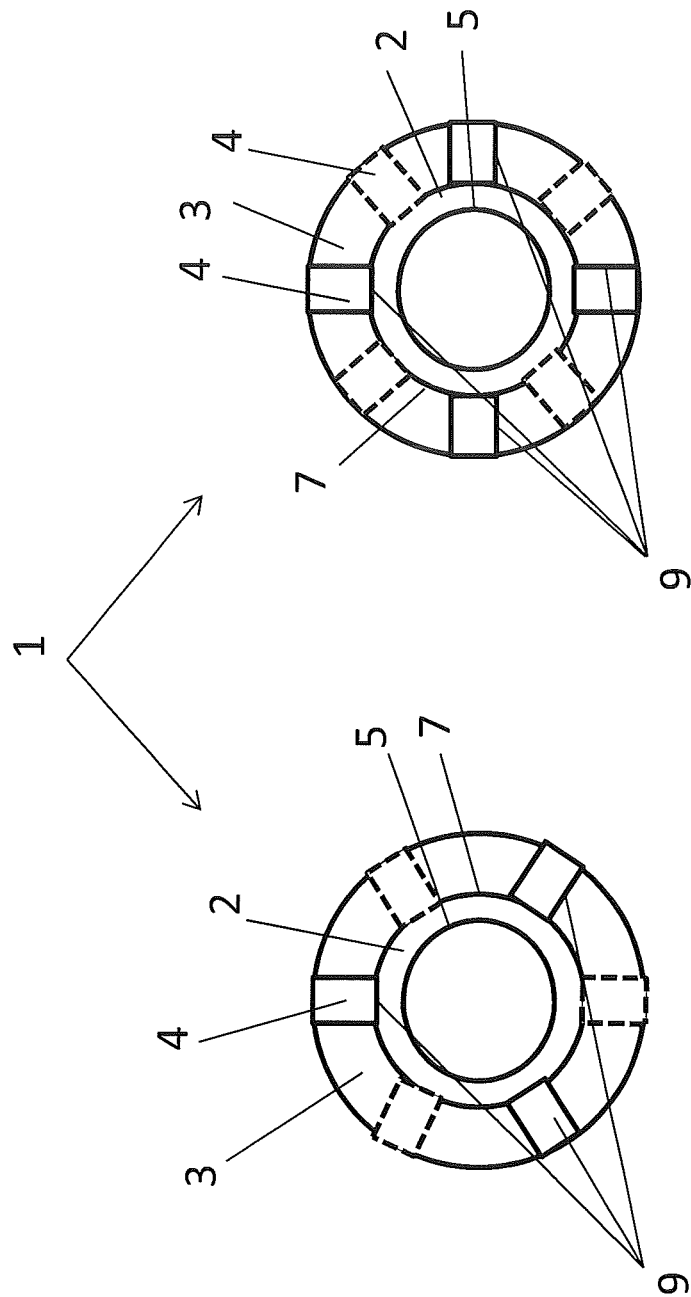
FIG. 4a, 4b are two schematic sectional views of a further embodiment of a fluid hose device.

FIGS. 4a and 4b are two schematic sectional views, each of an embodiment of a fluid hose device 1. FIG. 4a shows a fluid hose device 1 in which one group 9 comprises three connecting webs in each case, which webs are arranged so as to be offset from one another by 120° in each case. Two groups provided adjacently in the longitudinal direction of the fluid hose 2 are then arranged so as to be offset from one another by 60°, for example. The subsequent group of connecting webs is shown by dashed lines in FIG. 4a. FIG. 4b shows a fluid hose device 1, in which one group 9 comprises four connecting webs in each case, which webs are arranged so as to be offset from one another by 90° in each case. Two groups provided adjacently in the longitudinal direction of the fluid hose 2 are then arranged so as to be offset from one another by 45°, for example. The subsequent group of connecting webs 4 is shown by dashed lines in FIG. 4b.

Figure 5:
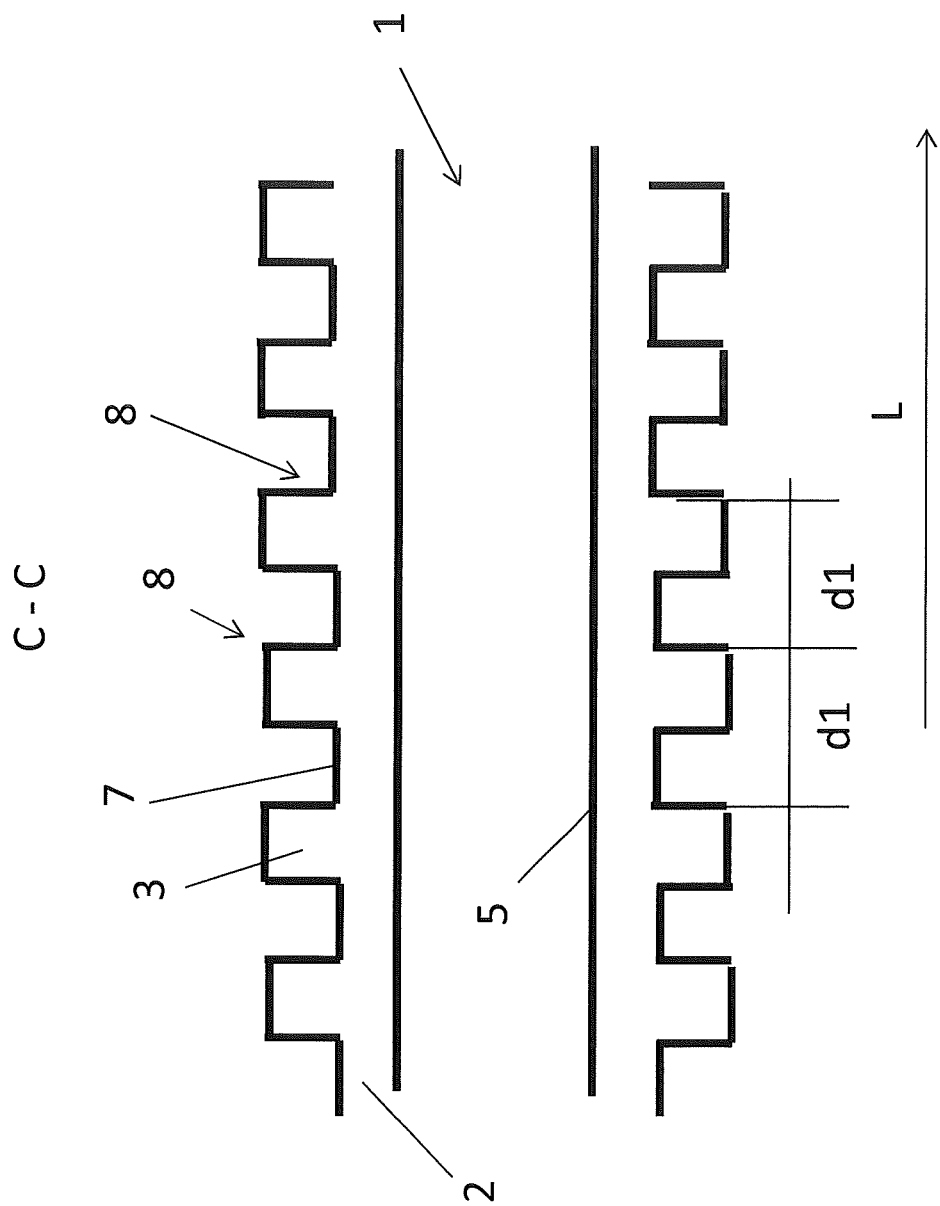
FIG. 5 is a schematic sectional view of an embodiment of a fluid hose device.

FIG. 5 is a schematic sectional view of an embodiment of a fluid hose device 1. The extension of the section C-C is shown in FIG. 3a. The anti-kink projections 3 form a comb-shaped pattern in the longitudinal direction L of the fluid hose. It can further be seen in this figure that the individual anti-kink projections 3 are at the same spacing dl from one another in each case.

Figure 6:
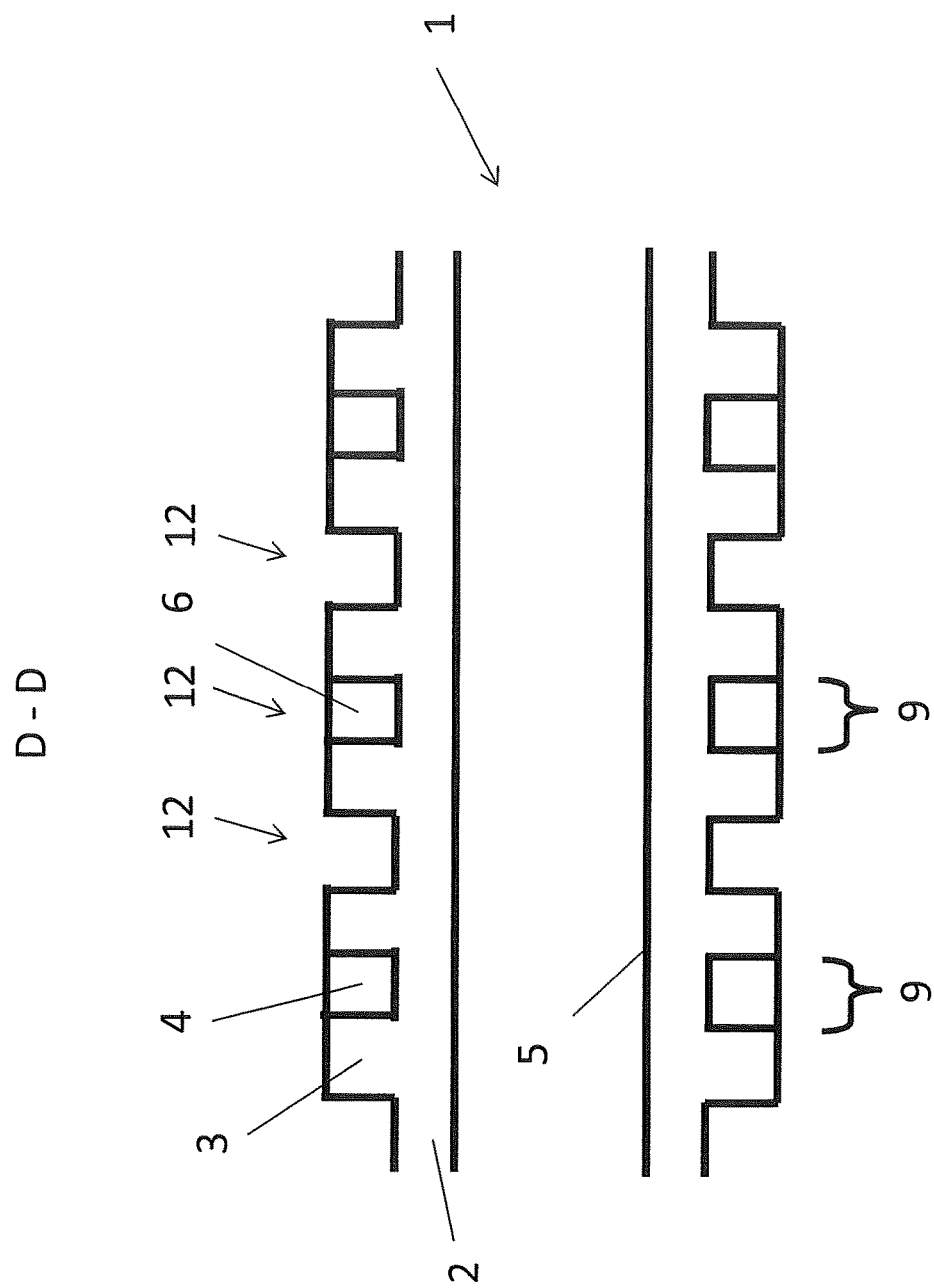
FIG. 6 is a schematic sectional view of an embodiment of a fluid hose device.

FIG. 6 is a schematic sectional view of an embodiment of a fluid hose device 1. The extension of the section D-D is shown in FIG. 3b, but this embodiment may differ from the embodiment shown in FIG. 3b. In FIG. 3b, the connecting webs comprise high-tensile-strength fibres 6, which increase the tensile strength of the connecting webs 4. The high-tensile-strength fibres 6 may be formed of a plastics material for example. However, glass fibres, aramid fibres, ceramic fibres or carbon fibres may also be used.

It is also possible, as can be seen in this embodiment, for the groups 9 of connecting webs to be provided between two anti-kink projections 3 in every other gap. It is also possible for the connecting webs 4 to be arranged only in every third gap or every fourth gap.

The fluid hose device 1 may be configured such that the fluid hose 2 is formed of a first plastics material and the anti-kink projections 3 and the connecting webs 4 are formed of a second plastics material which is different from the first plastics material. For example, the anti-kink projections and the connecting webs may be formed of a plastics material which has higher tensile strength compared with the first plastics material.

Moreover, as can be seen from FIG. 6 for example, the inside 5 of the fluid hose 2 is substantially planar. However, the inside 5 of the fluid hose 2 may also be provided with a pattern.

Figure 7:
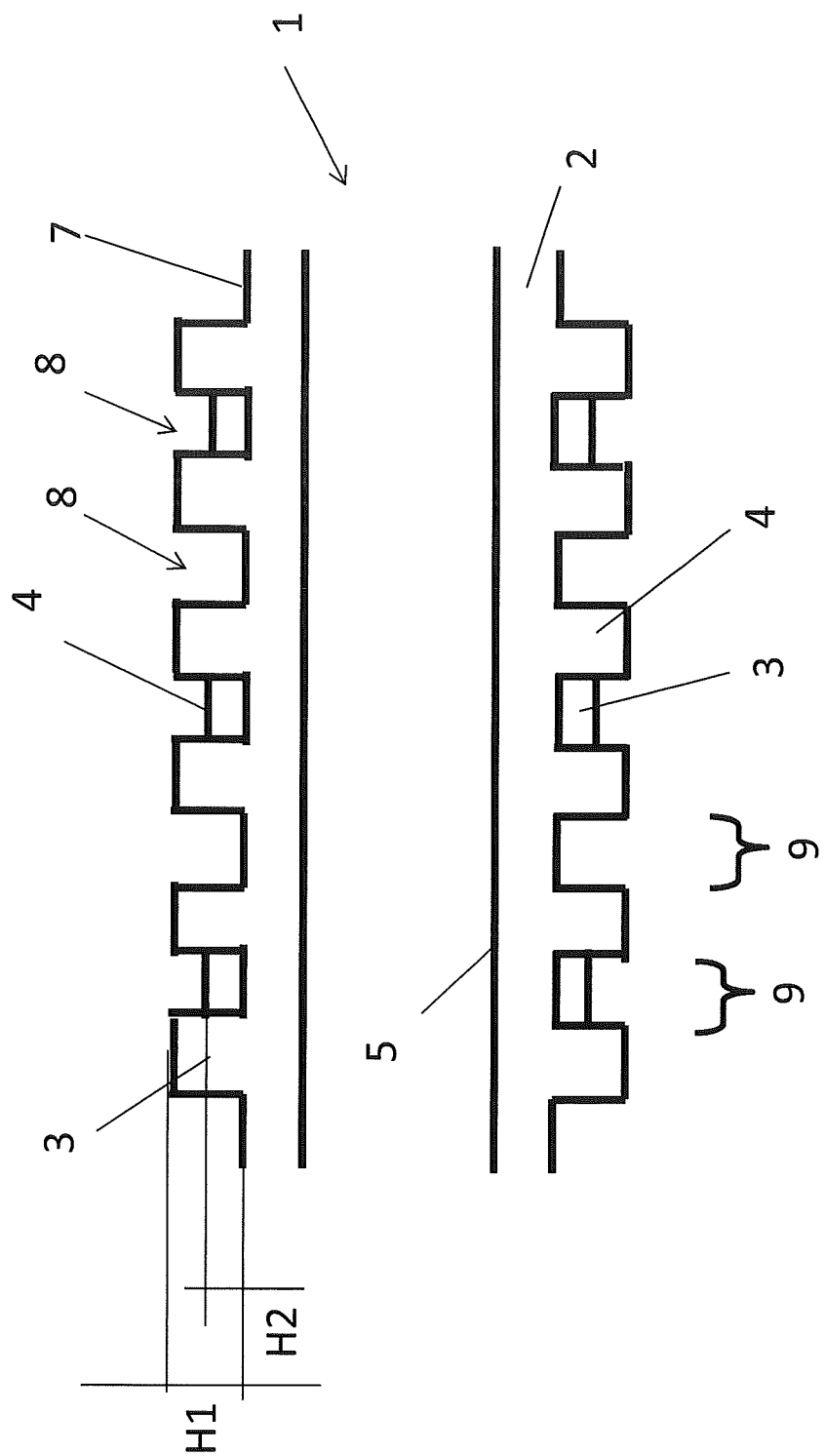
FIG. 7 is a schematic sectional view of a further embodiment of a fluid hose device.

FIG. 7 is a schematic sectional view of a further embodiment of a fluid hose device 1. In contrast to the embodiments shown in FIG. 1-6, in which the anti-kink projections 3, 11 and the connecting webs 4, 10 extend at the same height beginning at the external surface 7 of the fluid hose 2, the anti-kink projections 3, 11 and the connecting webs 4, 10 do not extend at the same height beginning at the external surface 7 of the fluid hose 2. It is thereby possible to adjust the flexibility and the dimensional stability to the respective constraints. The higher the connecting webs extend, the greater the dimensional stability of the fluid hose device 1.

In the embodiment shown, the connecting webs extend at a height H2 which is lower than the height H1 of the anti-kink projections.

Furthermore, in this embodiment, the anti-kink projections 3 and/or the connecting webs 4 have rounded outer sides. The service life of the fluid hose device can thereby be extended, since rounded outer sides are less susceptible to crack formation. The rounded outer sides may have a radius of from 0.1 mm to 2 mm for example, preferably 0.3 mm.

The anti-kink projections 3 and the connecting webs 4 are configured such that the fluid hose device 1 has angle-independent bending behaviour. This is achieved in that the connecting webs are provided in a regular pattern in the longitudinal direction L of the fluid hose device 1.

Figure 8:
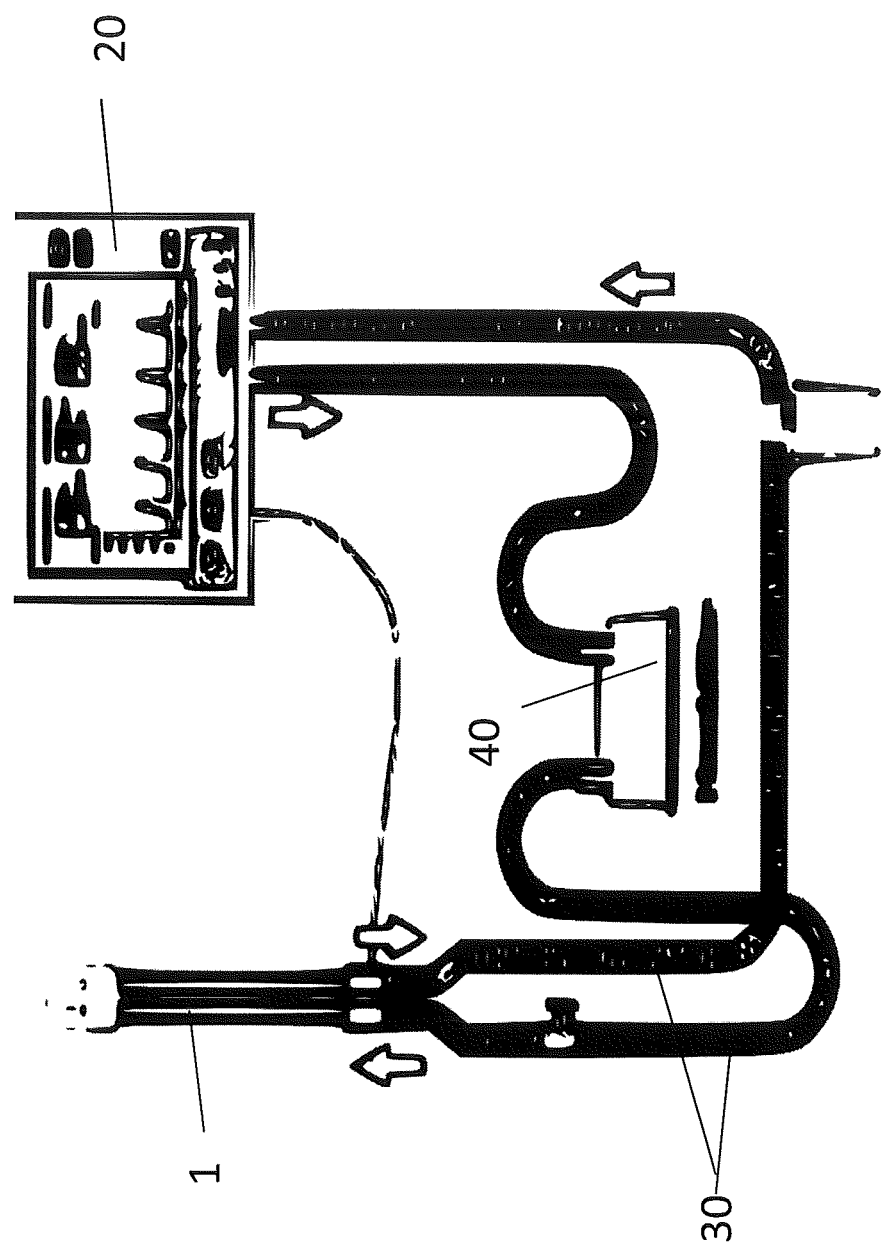
FIG. 8 is a schematic view of a CPAP ventilator comprising an embodiment of a fluid hose device.

FIG. 8 is a schematic view of a CPAP ventilator 20. The CPAP (continuous positive airway pressure) ventilator 20 is a form of ventilator and comprises different fluid lines 30 which can be configured in a manner similar to the fluid hose device 1 according to the invention. Furthermore, the CPAP machine 20 comprises a humidifier 40 which humidifies the respiratory gas. Moreover, the CPAP ventilator 20 comprises a fluid hose device 1 according to an embodiment of the present invention. The fluid hose device may be coupled to a respiratory mask for example, and may supply respiratory gas to or return respiratory gas from a patient via the respiratory mask.

Although the present invention has been fully described above with reference to preferred embodiments, it is not limited thereto, but can rather be modified in a number of ways.

LIST OF REFERENCE NUMERALS

1 Fluid hose device
2 Fluid hose
3 Anti-kink projections
4 Connecting webs
5 Inside of fluid hose
6 High-tensile-strength fibres
7 External surface of the fluid hose
8 Rounded corners
9 Group
10 Connecting webs
11 Anti-kink projections
12 Gaps
20 Ventilator
30 Fluid hoses
40 Humidifier

The invention claimed is:

1. A fluid hose device, comprising:
a fluid hose defining an inside surface that is substantially continuously circumferentially planar along a longitudinal direction of the fluid hose through which a fluid can be transported, said fluid hose further including a plurality of anti-kink projections integral and in one-piece with said inside surface, which are spaced apart from one another along the longitudinal direction of the fluid hose to define a gap between adjacent anti-kink projections, which projections extend in a circular manner around the external surface of the fluid hose, said projections defining a substantially constant outer diameter in the longitudinal direction; and groups of pluralities of connecting webs, wherein one of the groups of pluralities of connecting webs is provided in each gap between two adjacent anti-kink projections such that the connecting webs interconnect the adjacent anti-kink projections, wherein the groups are arranged with regard to one another in an alternating chevron pattern in the longitudinal direction of the fluid hose, and wherein the connecting webs have a projection height from the external surface of the fluid hose that is less than a projection height of the anti-kink projections from the external surface of the fluid hose, said fluid hose defining a radial cross-section that is substantially constant in the longitudinal direction along each group of pluralities of connecting webs.

2. The fluid hose device according to claim 1, wherein the groups comprise two connecting webs which are arranged so as to be offset from one another by 180°.

3. The fluid hose device according to claim 2, wherein the groups are arranged so as to be angularly offset by 90° in each case.

4. The fluid hose device according to claim 1, wherein the groups comprise n connecting webs, which are arranged so as to be offset from one another by 360°/n, n being a natural number greater than or equal to 3.

5. The fluid hose device according to claim 2, wherein the groups are arranged so as to be angularly offset by 360°/2n in each case, n being a natural number greater than or equal to 3.

6. The fluid hose device according to claim 1, wherein the connecting webs are integral and in one piece with the fluid hose.

7. The fluid hose device according to claim 1, wherein the anti-kink projections are arranged so as to be equidistant and in parallel.

8. The fluid hose device according to claim 1, wherein the fluid hose is a plastics material injection-molded part made of a thermoplastic.

9. The fluid hose device according to claim 1, wherein the connecting webs comprise high-tensile-strength fibers.

10. The fluid hose device according to claim 1, wherein the fluid hose is formed of a first plastics material and the connecting webs are formed of a second plastics material which is different from the first plastics material.

11. The fluid hose device according to claim 1, wherein the anti-kink projections and/or the connecting webs have rounded outer sides.

12. A ventilator, in particular a CPAP ventilator, including a fluid hose according to claim 1.

13. A fluid hose device, comprising:

a fluid hose defining an inside surface that is substantially continuously circumferentially planar along a longitudinal direction of the fluid hose through which a fluid can be transported, said fluid hose further including a plurality of anti-kink projections integral and in one-piece with said inside surface, which are spaced apart from one another along the longitudinal direction of the fluid hose, which projections extend in a circular manner around the external surface of the fluid hose, said projections defining a substantially constant outer diameter in the longitudinal direction; and groups of pluralities of connecting webs, wherein one of the groups of pluralities of connecting webs is provided in each gap between two adjacent anti-kink projections such that the connecting webs interconnect the adjacent anti-kink projections.

14. The fluid hose device according to claim 13, wherein the groups comprise two connecting webs which are arranged so as to be offset from one another by 180°.

15. The fluid hose device according to claim 14, wherein the groups are arranged so as to be angularly offset by 90° in each case.

16. The fluid hose device according to claim 13, wherein the groups comprise n connecting webs, which are arranged so as to be offset from one another by 360°/n, n being a natural number greater than or equal to 3.

17. The fluid hose device according to claim 14, wherein the groups are arranged so as to be angularly offset by 360°/2n in each case, n being a natural number greater than or equal to 3.

18. The fluid hose device according to claim 13, wherein the connecting webs are integral and in one piece with the fluid hose.

19. The fluid hose device according to claim 13, wherein the anti-kink projections are arranged so as to be equidistant and in parallel.

* * * * *